(12) United States Patent
McKay

(10) Patent No.: US 9,486,500 B2
(45) Date of Patent: Nov. 8, 2016

(54) OSTEOIMPLANT AND METHODS FOR MAKING

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 553 days.

(21) Appl. No.: 12/695,826

(22) Filed: Jan. 28, 2010

(65) Prior Publication Data
US 2011/0182963 A1    Jul. 28, 2011

(51) Int. Cl.
| | |
|---|---|
| *A61K 38/18* | (2006.01) |
| *A61F 2/28* | (2006.01) |
| *A61K 31/56* | (2006.01) |
| *A61K 38/30* | (2006.01) |
| *A61L 27/36* | (2006.01) |
| *A61L 27/42* | (2006.01) |
| *A61L 27/54* | (2006.01) |
| *A61K 35/28* | (2015.01) |
| *A61F 2/30* | (2006.01) |
| *A61F 2/44* | (2006.01) |
| *A61F 2/46* | (2006.01) |

(52) U.S. Cl.
CPC .............. *A61K 38/1875* (2013.01); *A61F 2/28* (2013.01); *A61K 31/56* (2013.01); *A61K 35/28* (2013.01); *A61K 38/1825* (2013.01); *A61K 38/1841* (2013.01); *A61K 38/1858* (2013.01); *A61K 38/30* (2013.01); *A61L 27/3608* (2013.01); *A61L 27/427* (2013.01); *A61L 27/54* (2013.01); *A61F 2/30965* (2013.01); *A61F 2/4455* (2013.01); *A61F 2002/2835* (2013.01); *A61F 2002/30009* (2013.01); *A61F 2002/30062* (2013.01); *A61F 2002/3096* (2013.01); *A61F 2002/30677* (2013.01); *A61F 2002/4495* (2013.01); *A61F 2002/4649* (2013.01); *A61F 2310/00359* (2013.01); *A61L 2300/222* (2013.01); *A61L 2300/402* (2013.01); *A61L 2300/406* (2013.01); *A61L 2300/41* (2013.01); *A61L 2300/414* (2013.01); *A61L 2300/44* (2013.01); *A61L 2300/64* (2013.01); *A61L 2430/02* (2013.01)

(58) Field of Classification Search
CPC ........... A61L 2430/02; A61L 27/3608; A61L 27/3683; A61L 27/3691; A61L 27/3847; A61L 31/005; A61L 27/3645; A61L 27/3641; A61L 27/3839; A61L 27/365; A61L 27/3695; A61L 2430/40; A61L 27/3604; A61F 2002/2835; A61F 2002/30009; A61F 2002/4495; A61F 2310/00359
See application file for complete search history.

(56) References Cited

U.S. PATENT DOCUMENTS

| | | | |
|---|---|---|---|
| 4,624,255 A | 11/1986 | Schenck et al. | |
| 4,742,054 A | 5/1988 | Naftchi | |
| 4,863,457 A | 9/1989 | Lee | |
| 5,263,984 A * | 11/1993 | Li et al. ..................... | 623/13.18 |
| 5,522,844 A | 6/1996 | Johnson | |
| 5,571,882 A | 11/1996 | Vetter | |
| 5,626,838 A | 5/1997 | Cavanaugh, Jr. | |
| 5,759,583 A | 6/1998 | Iwamoto et al. | |
| 5,868,789 A | 2/1999 | Huebner | |
| 5,942,241 A | 8/1999 | Chasin et al. | |
| 6,069,129 A | 5/2000 | Sandberg et al. | |
| 6,123,731 A | 9/2000 | Boyce et al. | |
| 6,179,862 B1 | 1/2001 | Sawhney | |
| 6,180,606 B1 * | 1/2001 | Chen et al. ................... | 424/422 |
| 6,248,345 B1 | 6/2001 | Goldenheim et al. | |
| 6,268,405 B1 | 7/2001 | Yao | |
| 6,287,588 B1 | 9/2001 | Shih et al. | |
| 6,326,020 B1 | 12/2001 | Kohane et al. | |
| 6,331,311 B1 | 12/2001 | Brodbeck et al. | |
| 6,428,804 B1 | 8/2002 | Suzuki et al. | |
| 6,440,444 B2 | 8/2002 | Boyce et al. | |
| 6,461,631 B1 | 10/2002 | Dunn et al. | |
| 6,524,607 B1 | 2/2003 | Goldenheim et al. | |
| 6,534,081 B2 | 3/2003 | Goldenheim et al. | |
| 6,589,549 B2 | 7/2003 | Shih et al. | |
| 6,616,946 B1 | 9/2003 | Meier et al. | |
| 6,630,155 B1 | 10/2003 | Chandrashekar et al. | |
| 6,632,457 B1 | 10/2003 | Sawhney | |
| 6,652,883 B2 | 11/2003 | Goupil et al. | |
| 6,676,971 B2 | 1/2004 | Goupil et al. | |
| 6,696,073 B2 * | 2/2004 | Boyce et al. ................. | 424/422 |
| 6,710,126 B1 | 3/2004 | Hirt et al. | |
| 6,723,741 B2 | 4/2004 | Jeon et al. | |
| 6,723,814 B2 | 4/2004 | Meier et al. | |
| 6,756,058 B2 | 6/2004 | Brubaker et al. | |
| 6,773,714 B2 | 8/2004 | Dunn et al. | |
| 6,843,807 B1 | 1/2005 | Boyce et al. | |

(Continued)

FOREIGN PATENT DOCUMENTS

| | | | |
|---|---|---|---|
| WO | WO96/39203 | * | 12/1996 |
| WO | 03005961 A2 | | 1/2003 |

(Continued)

OTHER PUBLICATIONS

Williams Biomaterials, Aug. 2005;26(23):4817-27.*

(Continued)

*Primary Examiner* — Anoop Singh
(74) *Attorney, Agent, or Firm* — Sorell Lenna & Schmidt LLP

(57) ABSTRACT

An osteoimplant is disclosed and includes a plurality of partially demineralized fibers. Each fiber has an elongated, thin body having a length of about 1 centimeter to about 3 centimeters. Further, the plurality of fibers engages to establish a matrix of material. The disclosure is further directed to a method of making the above-mentioned osteoimplant.

13 Claims, No Drawings

(56) References Cited

U.S. PATENT DOCUMENTS

| | | |
|---|---|---|
| 6,863,694 B1 | 3/2005 | Boyce et al. |
| 6,921,541 B2 | 7/2005 | Chasin et al. |
| 6,974,462 B2 | 12/2005 | Sater |
| 7,045,141 B2 | 5/2006 | Merboth et al. |
| 7,070,809 B2 | 7/2006 | Goupil et al. |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 7,658,765 B2 | 2/2010 | Lambrecht et al. |
| 8,008,357 B2 * | 8/2011 | Shoji et al. .............. 516/103 |
| 2002/0009454 A1 | 1/2002 | Boone et al. |
| 2002/0090398 A1 | 7/2002 | Dunn et al. |
| 2002/0122771 A1 | 9/2002 | Holland et al. |
| 2003/0022927 A1 | 1/2003 | Jeon et al. |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0072799 A1 | 4/2004 | Li et al. |
| 2004/0082540 A1 | 4/2004 | Hermida Ochoa |
| 2004/0109893 A1 | 6/2004 | Chen et al. |
| 2004/0146543 A1 * | 7/2004 | Shimp ............ A61L 27/3608 424/423 |
| 2004/0214793 A1 | 10/2004 | Hermida Ochoa |
| 2005/0059744 A1 | 3/2005 | Donello et al. |
| 2005/0129656 A1 | 6/2005 | Goupil et al. |
| 2005/0142163 A1 | 6/2005 | Hunter et al. |
| 2005/0175709 A1 | 8/2005 | Baty, III et al. |
| 2005/0186261 A1 | 8/2005 | Avelar et al. |
| 2005/0197293 A1 | 9/2005 | Mellis et al. |
| 2005/0222684 A1 | 10/2005 | Ferree |
| 2005/0240269 A1 | 10/2005 | Lambrecht et al. |
| 2005/0287218 A1 | 12/2005 | Chaouk et al. |
| 2005/0288789 A1 | 12/2005 | Chaouk et al. |
| 2006/0030948 A1 | 2/2006 | Manrique et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2007/0004790 A1 | 1/2007 | Chow et al. |
| 2007/0093907 A1 | 4/2007 | Goupil et al. |
| 2007/0150061 A1 | 6/2007 | Trieu |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2007/0254041 A1 * | 11/2007 | Drapeau et al. .............. 424/550 |
| 2008/0021074 A1 | 1/2008 | Cartt |
| 2008/0058953 A1 | 3/2008 | Scarborough |
| 2008/0091207 A1 | 4/2008 | Truckai et al. |
| 2008/0097229 A1 | 4/2008 | Roy et al. |
| 2008/0147197 A1 * | 6/2008 | McKay .................... 623/23.51 |
| 2008/0188945 A1 | 8/2008 | Boyce et al. |
| 2008/0269717 A1 | 10/2008 | Crandall et al. |
| 2009/0020076 A1 | 1/2009 | Ghiraldi |
| 2009/0155378 A1 | 6/2009 | Behnam et al. |
| 2009/0222096 A1 | 9/2009 | Trieu |
| 2009/0264489 A1 | 10/2009 | Zanella |
| 2009/0275913 A1 | 11/2009 | Trieu |

FOREIGN PATENT DOCUMENTS

| | | | |
|---|---|---|---|
| WO | 2005034998 A2 | | 4/2005 |
| WO | WO2005097217 | * | 10/2005 |
| WO | 2007005177 A1 | | 1/2007 |
| WO | 2007076272 | | 7/2007 |

OTHER PUBLICATIONS

Murphy et al Cell Adh Migr. 2010 Jul.-Sep.; 4(3): 377-381.*

Atrigel, QTL, Inc. Drug Delivery Platform, Jul. 2006 revision,QTL USA, Inc. Fort Collins, CO.

Medline, Pharmacological Approaches: http://www.medscape.com/viewarticle/552267_3.

Elizabeth A. Moberg-Wolff, M.D.; emedicine Article-Spasticity pp. 1-15.

Daniel P. Moore, M.D.; Helping your patients with spasticity reach maximal function, Aug. 1998, pp. 1-9, vol. 104, No. 2. http://www.postgraduate.com/issue/1998/08_98/moore,htm.

Kyphon, Enhanced Discyphor Catheter System, Kyphon Inc. 2007, Sunnyvale, CA.

Skedros, John G. et al. "The influence of collagen fiber orientation and other histocompositional characteristics on the mechanical properties of equine cortical bone," Journal of Experimental Biology, Aug. 1, 2006, 209:3025-3042.

* cited by examiner

OSTEOIMPLANT AND METHODS FOR MAKING

FIELD OF THE DISCLOSURE

The present disclosure relates generally to orthopedics and orthopedic surgeries. More specifically, the present disclosure relates to materials and methods for treating bone voids.

BACKGROUND

Grafts that aid in the healing of damaged bone are a relatively old technology that has undergone substantial growth in light of recent advances in medicine and biology. Improved understanding of osteoinductive and osteoconductive properties of certain materials has enabled the design of implants of ever-increasing efficacy. Recent examples include U.S. Pat. No. 7,045,141 to Merboth et al., entitled "Allograft Bone Composition Having a Gelatin Binder"; U.S. Pat. No. 6,808,585 to Boyce et al., entitled "Osteogenic Implant Derived From Bone"; U.S. Pat. No. 6,548,080 to Gertzman et al., entitled "Method for Partially Demineralized Cortical Bone Constructs"; and U.S. Pat. No. 6,776,800 to Boyer, II et al., entitled "Implants Formed with Demineralized Bone". Absorbable Collagen Sponge ("ACS"), by Integra LifeSciences Corporation (Plainsboro, N.J.), and Mastergraft® Matrix, by Medtronic Sofamor Danek (Memphis, Tenn.), are specific examples of grafts currently available on the market.

Many of these implants do not provide any structural support at the implant site. Structural support ranges from the ability to resist the tendency for compression of the graft by local tissues (space maintenance) to the ability to be weight bearing. There exist numerous situations in which it is desirable to have an implant that both aids in the re-growth of the bone at the implant site while also providing structural support, which are so-called structural implants. However, not all structural implants have the properties, such as compression resistance, necessary for certain applications.

Accordingly, it is desirable to provide an osteoimplant that provides structural capabilities, yet which provides superior osteoinductive, osteoconductive and re-absorption properties.

SUMMARY

In a particular embodiment, an osteoimplant includes a plurality of partially demineralized fibers. Each fiber has an elongated, thin body having a length of about 1 centimeter to about 3 centimeters. The plurality of fibers engage to establish a matrix of material.

In an embodiment, a method of making an osteoimplant is provided. The method includes partially demineralizing a bone to form a plurality of fibers, wherein each fiber comprises an elongated, thin body having a length of about 1 centimeter to about 3 centimeters; and forming the plurality of partially demineralized fibers into a fiber matrix.

DETAILED DESCRIPTION

A matrix material is disclosed that can be used as an osteoimplant. In a particular embodiment, the matrix material includes a plurality of fibers. Typically, each fiber has an elongated, thin body. In an embodiment, the plurality of fibers engage to form the matrix material. In a particular embodiment, the plurality of fibers have a length of about 1 centimeters to about 3 centimeters, such as about 1 centimeters to about 2 centimeters. The length of the fibers enables the matrix material to form and, in an exemplary embodiment, the length of the fibers are spatially arranged in a random-orientation. In particular, the length and random-orientation of the plurality of fibers enable the formation of an osteoimplant with desirable physical and mechanical properties. For instance, the length of the fibers and random-orientation is advantageous to form a superior osteoimplant that is compression resistant, has a desirable degradation rate, and is osteoinductive. "Osteoinductive" as used here refers to fibers that promote bone growth throughout the internal structure of the implant.

In an embodiment, the source of the fibers can be allogenic, xenogenic, autogenic, recombinant, or any combination thereof. In a particular embodiment, the plurality of fibers are obtained from an allogenic source such as, for instance, an allograft bone segment. Any allograft bone segment is appropriate that may provide fibers of the length described above. In an exemplary embodiment, the allograft bone segment may be derived from long bone sites such as the humerus, radius, ulna, femur, tibia, fibula, the bones of the hands or feet including the metacarpals, metatarsals, or phalanges, or bones from the spine, pelvis or other location. In a particular embodiment, the allograft bone segment can be machined into strips. In another embodiment, the bone segment is partially demineralized and then the fibers are machined from the partially demineralized allograft bone segment. Any reasonable method is envisioned to machine the allograft bone segment. The strips may be of any length to provide fibers having a length as described above.

In an embodiment, the allograft bone strips or allograft bone segment are partially demineralized. The term "partial demineralization" means that from about 5% to about 90% of the original mineral content of the bone segment has been removed. The amount of demineralization of the bone segment typically depends upon the desired properties of the final osteoimplant. In a particular embodiment, the partial demineralization removes about 20% to about 90%, such as about 30% to about 90%, or even about 40% to about 90% of the original mineral content from the allograft strips. The partial demineralization provides a corresponding osteoinductive matrix that has greater compression resistance than a fully demineralized fiber matrix. In a particular embodiment, the osteoimplant of the present invention is free of any fully demineralized fibers or particles.

Methods that provide for the partial demineralization of bone segment are known, and broadly involve chemically processing the bone with hydrochloric acid, chelating agents, electrolysis or performing other treatments to remove all or a portion of the minerals contained within the natural bone, leaving behind fibers having the length as defined above which form into the randomly-orientated matrix. In an embodiment, the partially demineralized fibers may be entangled in the random-orientation by any reasonable means. In an example, the partially demineralized fibers may be mechanically entangled.

In an exemplary embodiment, the fibers are chemically crosslinked after partial demineralization. In a particular embodiment, the chemical crosslinking both stiffens and bonds the fibers together. Accordingly, the use of a chemical crosslinker may further increase the compression resistance of the resulting osteoimplant. Any reasonable chemical crosslinker may be used to crosslink the fibers. In a particular embodiment, the cross-linking agent can be glutaraldehyde, genipin, formaldehyde, 1-Ethyl-3-(3-dimethylaminopropyl)-carbodiimide/N-hydroxysuccinimide (EDC/NHS), or any combination thereof. Further, the cross-linking agent can be another protein cross-linking agent.

In an embodiment, any number of additives may be included within the matrix. Any reasonable additive may be included that can be envisioned for an osteoimplant. For example, the additives can include radiocontrast media, drugs, cellular matters, biological factors, or any combination thereof. In a particular embodiment, the drugs can include, for example, antibiotics, analgesics, anti-inflammatory drugs, anti-TNF-alpha, steroids, or any combination thereof. Further, the cellular matters can include, for example, bone marrow derived stem cells, lipo derived stem cells, or any combination thereof. The biological factor can include, for example, bone morphogenetic protein (BMP), growth differentiation factor (GDF), cartilage-derived morphogenetic protein (CDMP), platelet derived growth factor (PDGF), insulin-like growth factor (IGF), LIM mineralization protein, fibroblast growth factor (FGF), osteoblast growth factor, or any combination thereof. The additives can also include additives to promote matrix formation. Additives may improve protein retention, reduce protein degradation, promote protein folding, promote water binding, promote protein-to-protein interaction, promote water immobilization, or any combination thereof. Additionally, the additives can include polysaccharides such as, for example, proteoglycans, hyaluronic acid, or combination thereof, which can attract or bind water to increase hydration of the osteoimplant site. Further additives can include osteoinductive agents. In a particular embodiment, the osteoinductive agents have bone morphogenic protein (BMP) binding capability to partially demineralized fibers, minerals, collagen, and the like. In an embodiment, the additives include demineralized bone matrix (DBM particles), ceramic particles, or combinations thereof. Any reasonable means or methods can be used to include the additive within the matrix.

In an embodiment, the matrix may be "remineralized" to precipitate mineral back onto the partially demineralized fibers. Any reasonable method may be employed to remineralize the matrix. For instance, a mineral bath can be used to provide precipitation of mineral back onto the partially demineralized fibers. The mineral and concentration thereof to remineralize the matrix can be determined based on the properties desired. In an embodiment, any appropriate mineral may be envisioned that increases the matrix stiffness, increases the osteoconductivity of the partially demineralized fibers, or combination thereof. In an exemplary embodiment, the crosslinked matrix is placed into a mineral bath of calcium salts, silicate, or combination thereof.

Once the matrix of partially demineralized fibers has been provided, the matrix may be impregnated with a slurry to provide an open porous structure throughout an internal structure of the matrix. In an embodiment, the slurry may include collagen, or any other natural or synthetic polymer envisioned. For instance, the slurry may include chitosan, hyaluronic acid, alginate, gelatin, silk, elastin, polylactic and/or lactic acid, the like, and combinations thereof. In an embodiment, the collagen may be in a solution of any reasonable concentration and particle/fiber size to provide the open porous structure of collagen throughout the internal structure of the matrix. For instance, the open porous structure creates an increase of the surface area for cell attachment and new osteoid formation once the matrix is placed at the site of the osteoimplant. Any reasonable solution may be used for the slurry. In a particular embodiment, water or a saline solution, for example, may be used to form the slurry. Materials which are sticky in texture may also assist in the adherence of the collagen to the matrix.

Any reasonable method may be employed to impregnate the matrix with the slurry. This slurry may be coated over the matrix or the matrix may be submersed partially or wholly into the slurry. The matrix may optionally be vibrated, rotated, centrifuged, or combination thereof to encourage the slurry to migrate into the matrix. In an embodiment, it may be desirable to subject the matrix to at least a mild vacuum to partially or wholly evacuate the air from the matrix. In an embodiment, the slurry further includes any reasonable ceramic or bone particles that have osteoconductivity properties. Exemplary ceramic particles include calcium phosphates, tricalcium phosphate, hydroxyapatite, silicate containing ceramics, and combinations thereof.

In an embodiment, the addition of the slurry to the matrix is followed by freeze-drying of the slurry in the matrix. Typical freeze-drying is achieved through the use of standard commercial freeze-drying equipment. In a particular embodiment, the freeze-drying of the collagen slurry in the matrix facilitates the formation of a porous structure throughout the internal structure of the matrix. The pores formed through the internal structure of the matrix may be of any reasonable size to facilitate cell attachment and new osteoid formation when the matrix is placed at the site of the osteoimplant. In an embodiment, the allograft fiber matrix can have pores of about 1.0 to about 5.0 mm diameter in size. In an embodiment, the addition of the collagen slurry provides a collagen matrix with pores large enough to allow cell migration in, such as having pores greater than about 0.01 mm diameter. In a particular embodiment, the collagen slurry after freeze drying can have pores about 0.01 mm to about 3.0 mm diameter in size.

The formation of the osteoimplant further includes cutting the matrix material into the final desired shape. The desired shape is dependent upon the site of implantation. In an embodiment, the osteoimplant may be pre-shaped for a specific target region or may be provided in a standard shape that may be later tailored by the physician for the particular requirements of the implant site. Any suitable method may be used to shape the osteoimplant and may be performed before or after the matrix is formed. Typically, the osteoimplant may be cut with any reasonable medical or surgical tool such as a saw, file, blade, and the like.

Processing of the matrix may be performed under aseptic conditions such that the final osteoimplant is sterile and does not require a terminal sterilization procedure. Alternatively, the matrix may be processed under less rigorous conditions and terminal sterilization is used to achieve sterility. Various methods of terminal sterilization may be used (such as gamma or electron beam irradiation, ethylene oxide, etc.), but should be controlled to ensure the final osteoimplant maintains appropriate biological characteristics for supporting bone growth.

Generally, the matrix, including the partially demineralized fibers and optional collagen and additives form the osteoimplant. The amount of partial demineralization and any optional additives may be chosen depending upon the properties desired for the osteoimplant. In some embodiments, the matrix consists essentially of the partially demineralized fibers as described above. As used herein, the phrase "consists essentially of" used in connection with the matrix of the osteoimplant precludes the presence of materials that affect the basic and novel characteristics of the osteoimplant, although, various additives as described above, such as chemical crosslinkers, collagen, and the above discussed additives, may be used in the osteoimplant.

It is expected that the matrix may be used as an osteoimplant that will have utility in a diverse array of procedures where bone grafting is desired. Exemplary procedures include posterolateral spinal fusion, interbody spine fusion, fracture repair, bone cyst filling, periodontal, cranial, containment of autograft, maxillofacial, and other procedures where bone grafting is desirable. In an embodiment, the osteoimplant may be used for long bone segmental defects, alveolar bone ridge grafting, repairing calvarial bone defects, and the like.

Once formed into a matrix, the matrix exhibits mechanical properties that advantageously enhance the performance of the osteoimplant formed of the matrix. In particular, the osteoimplant may exhibit desirable mechanical properties, such as compression resistance. In an exemplary embodiment, the hydrated matrix exhibits a compression resistance of at least about 2 MPa, for example, measured using standard compression test methods. In particular, the compression resistance may be at least about 5 MPa, such as at least about 10 MPa, or even at least about 15 MPa. In a particular embodiment, the compression resistance provides an osteoimplant that withstands drilling during a surgical procedure. For instance, any type of screws, spikes, and the like may be used to fasten the osteoimplant within the implant site.

In addition, the osteoimplant may be evaluated for performance in producing characteristics desirable for the osteoimplant such as, for example, the matrix retaining its shape and structure for several weeks after implantation. In an exemplary embodiment, the matrix exhibits a degradation rate of at least about 20% six months after implantation. In particular, the degradation rate may be at least about 30% six months after implantation, such as at least about 40% six months after implantation, or even at least about 50% six months after implantation. The degradation rate is desirable for providing structural integrity at the implantation site while bone growth occurs throughout the internal structure of the matrix.

Further, the osteoimplant is osteoinductive and is an ideal bone grafting matrix. For instance, bone growth replaces at least about 20% of the implant after six months implantation, such as at least about 30% of the implant after six months implantation. In a particular embodiment, the osteoimplant is osteoinductive, compression resistant, and has an exemplary degradation rate. For instance, the osteoinductive osteoimplant has a compression resistance of at least about 2 MPa, a degradation rate of at least about 20% six months after implantation, and bone growth replacing at least about 20% of the implant after six months implantation. Accordingly, the osteoinductive osteoimplant is highly compression resistant, retains its shape and structure, and promotes bone growth throughout the matrix.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An osteoimplant comprising: a plurality of partially demineralized bone fibers in a remineralized matrix material, wherein each fiber has an elongated, thin body having a length of about 1 centimeter to about 3 centimeters, wherein the plurality of partially demineralized bone fibers are chemically crosslinked with a chemical cross-linker, wherein plurality of fibers engage to establish the matrix material, the matrix material having a porous structure throughout the internal structure of the matrix having pores of about 3.0 mm to about 5.0 mm diameter, and the osteoimplant has a compression resistance of about 10 MPa, and the length of the fibers are spatially arranged in a random-orientation, and the matrix comprises collagen dispersed within an internal structure of the matrix.

2. The osteoimplant of claim 1, wherein the partially demineralized fibers are formed from an allogenic source.

3. The osteoimplant of claim 1, wherein the partially demineralized fibers have about 20% to about 90% of an original mineral content removed.

4. The osteoimplant of claim 1, wherein the chemical crosslinker includes glutaraldehyde, genipin, formaldehyde, 1-Ethyl-3-(3-dimethylaminopropyl) carbodiimide/N-hydroxysuccinimide (EDC/NHS), or a combination thereof.

5. The osteoimplant of claim 1, further comprising an osteoconductive mineral salt incorporated within the matrix material.

6. The osteoimplant of claim 5, wherein the osteoconductive mineral salt is calcium salt.

7. The osteoimplant of claim 1, having a degradation rate of about 20% six months after implantation.

8. The osteoimplant of claim 1, wherein the collagen is a freeze-dried collagen.

9. The osteoimplant of claim 8, wherein the freeze-dried collagen further comprises osteoconductive ceramic particles.

10. The osteoimplant of claim 1, further comprising an additive.

11. The osteoimplant of claim 10, wherein the additive comprises a radiocontrast medium, a drug, a cellular matter, a biological factor, or a combination thereof.

12. The osteoimplant of claim 11, wherein the drug comprises an antibiotics, an analgesics, an anti-inflammatory drugs, an anti-TNF-alpha, a steroid, or a combination thereof.

13. The osteoimplant of claim 11, wherein the biological factor comprises bone morphogenetic protein (BMP), growth differentiation factor (GDF), platelet derived growth factor (PDGF), insulin-like growth factor (IGF), LIM mineralization protein, fibroblast growth factor (FGF), osteoblast growth factor, or a combination thereof.

* * * * *